US00PP31334P2

(12) United States Plant Patent
Van Dijk

(10) Patent No.: US PP31,334 P2
(45) Date of Patent: Jan. 7, 2020

(54) ***ANTHURIUM* PLANT NAMED 'ANTHYQDAL'**

(50) Latin Name: ***Anthurium andraeanum* L.**
Varietal Denomination: ANTHYQDAL

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,052

(22) Filed: Sep. 19, 2018

(51) Int. Cl.
*A01H 5/02* (2018.01)

(52) U.S. Cl.
USPC ..... Plt./365

(58) Field of Classification Search
USPC ..... Plt./365, 366, 367
CPC ... A01H 5/02; A01H 5/00; A01H 5/12; A01H 6/00; A01H 6/10
See application file for complete search history.

(56) References Cited

U.S. PATENT DOCUMENTS

PP30,527 P2 * 5/2019 Van Dijk ..... Plt./365

OTHER PUBLICATIONS

Upov Pluto Plant Variety Database Jun. 21, 2019, retrieved on Jun. 24, 2019, retrieved from the Internet at www.upov.int/pluto/en/index.jsp, one page. (Year: 2019).*

EU Community Plant Variety Rights Application No. 2016/2943, Application n°A201603027, filed Nov. 25, 2016, 8 pages.

EU Community Plant Variety Office Official Gazette, Jan. 2017, Feb. 15, 2017, cover page and pp. 30, 51.

EU Community Plant Variety Rights Certificate on the Grant, EU 49867, Jul. 2, 2018, 2 pages.

* cited by examiner

*Primary Examiner* — June Hwu

(74) *Attorney, Agent, or Firm* — Jondle & Associates, P.C.

(57) ABSTRACT

A new *Anthurium* plant named 'ANTHYQDAL' particularly distinguished by having shiny, white with light pink shade and slightly green margins, ovate and durable spathes that retain the original color for a very long period of time, purplish pink spadices with reddish brown tips, dark green and ovate cordate leaves, early and rich flowering continuously throughout the year, and a plant height of 27.0 cm to 32.0 cm is disclosed.

3 Drawing Sheets

Genus and species: *Anthurium andraeanum* L.
Variety denomination: 'ANTHYQDAL'.

BACKGROUND OF THE NEW PLANT

The present invention comprises a new and distinct variety of *Anthurium*, botanically known as *Anthurium andraeanum* L., and hereinafter referred to by the variety name 'ANTHYQDAL'. The new *Anthurium* plant is a product of a planned breeding program conducted by the inventor in Bleiswijk, the Netherlands. The objective of this breeding program was to create a new 27.0 cm to 32.0 cm height plant with shiny, wavy, white cordate spathes with light pink shade.

The new variety originated from a cross-pollination made in December 2001 in Bleiswijk, The Netherlands. The female parent was a red *Anthurium* pot plant designated 'ANTHEPEDI' (U.S. Plant Pat. No. 18,644), and the male parent was a white *Anthurium* pot plant designated '632-06' (unpatented).

A single plant was selected from the progeny of the stated cross in February 2012 and has been asexually reproduced repeatedly by meristem tissue culture in Bleiswijk, The Netherlands over a 6-year period. The present invention has been found to retain its distinctive characteristics through successive asexual propagations.

Plant Breeder's Rights for this variety have been applied for in the European Union on Nov. 25, 2016. 'ANTHYQDAL' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Shiny, wavy, white ovate spathe with light pink shade and slightly green margins;
2) Purplish pink spadix with reddish brown tip; and
3) Green, ovate cordate leaves.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 34-week old plant grown in a greenhouse in Bleiswijk, The Netherlands in July 2018. Colors in the photographs may differ from the color values cited in the detailed botanical description, which accurately describe the actual colors of the new variety.

DESCRIPTION OF THE NEW VARIETY

Figure 1:
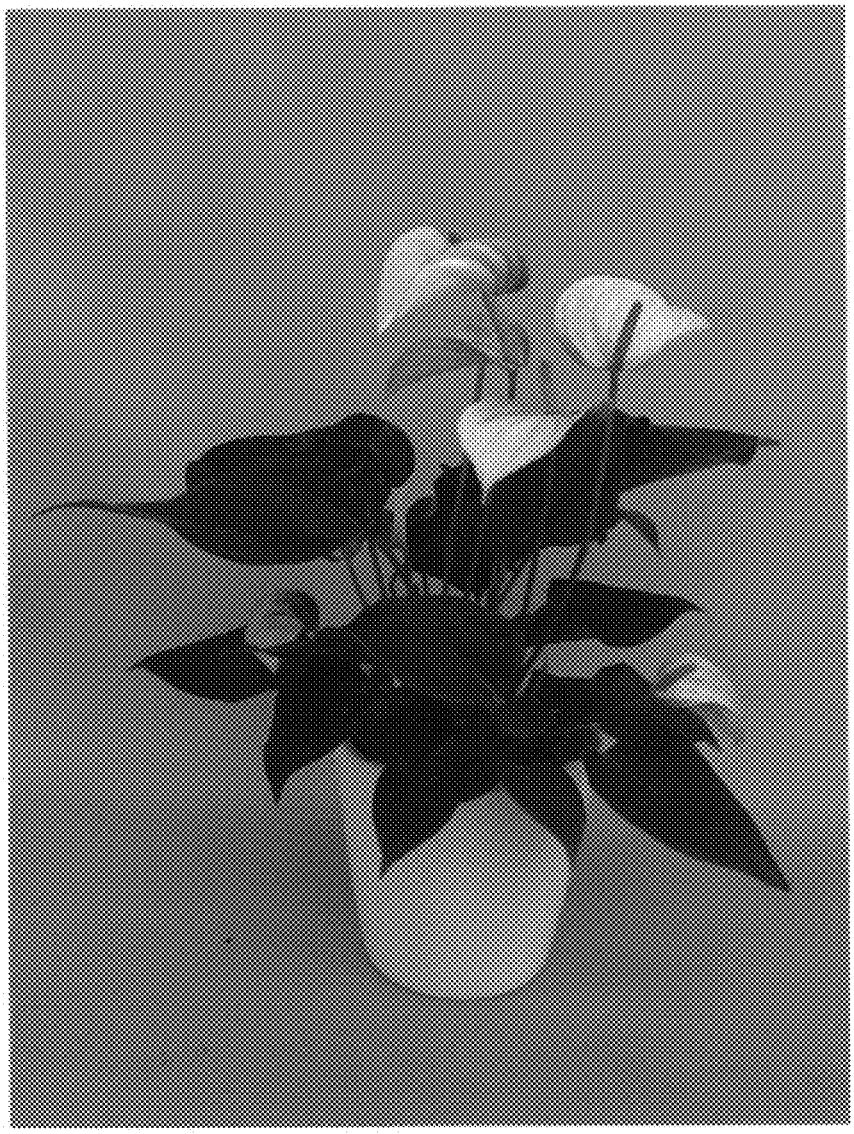
FIG. 1 shows the overall plant habit, including blooms, buds and foliage.
Figure 2:
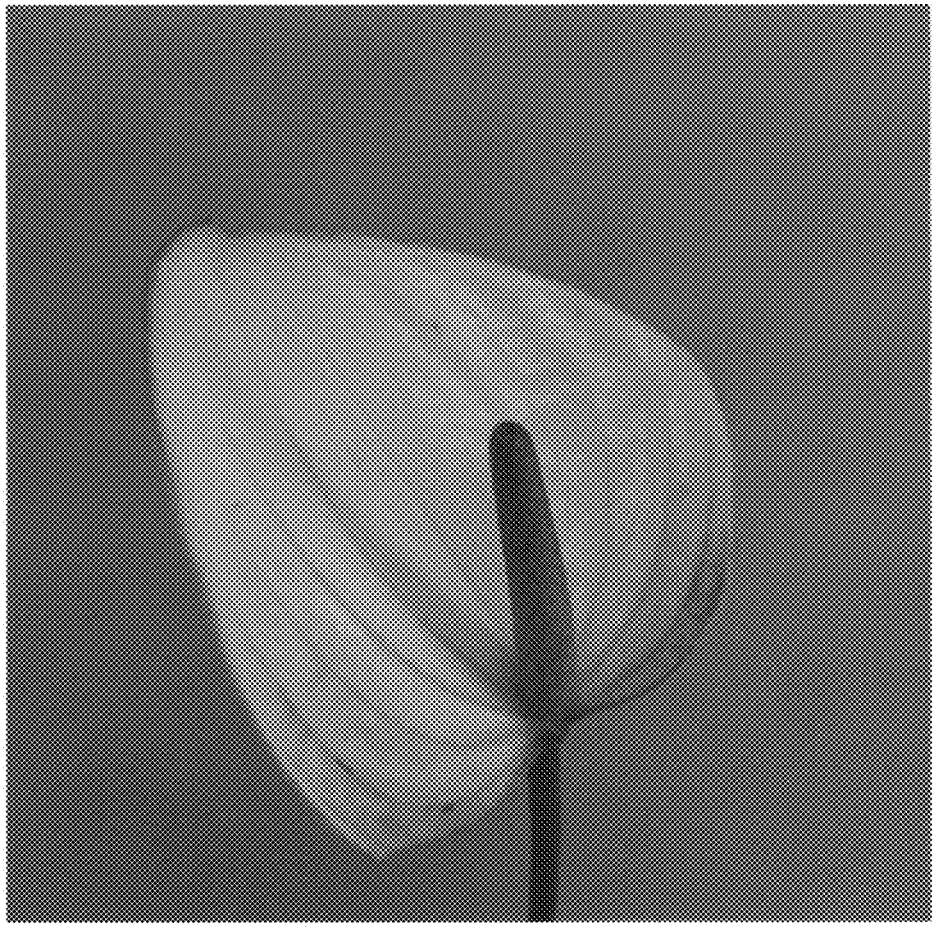
FIG. 2 shows a close-up of the mature spathe.
Figure 3:
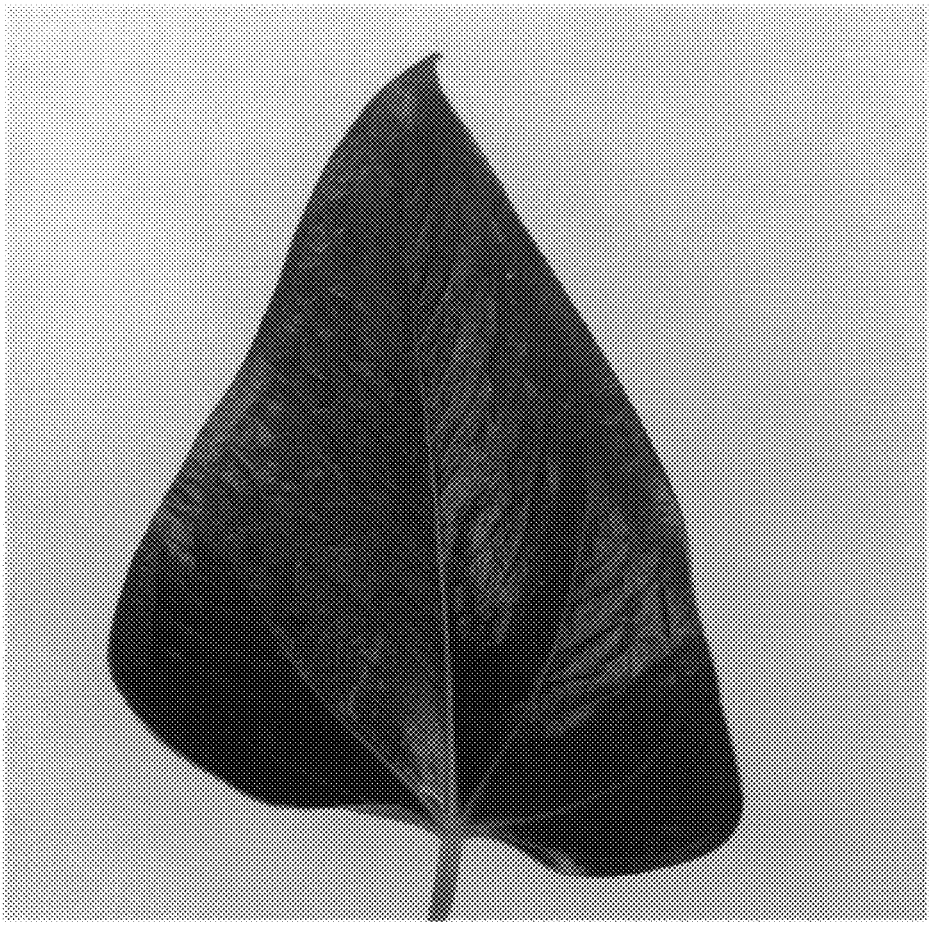
FIG. 3 shows a close-up of the upper leaf blade surface.

The following detailed description sets forth the distinctive characteristics of 'ANTHYQDAL'. The data which define these characteristics were collected from asexual reproductions carried out in Bleiswijk, The Netherlands. The plant history was taken on 34-week old plants which were planted from tissue culture in 12 centimeter (diameter) pots and grown in a glass greenhouse between 19° C. and 24° C. Observations were made in July 2018. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHYQDAL'.

Parentage:

*Female parent*.—*Anthurium* plant 'ANTHEPEDI' (U.S. Plant Pat. No. 18,644).

*Male parent*.—*Anthurium* plant '632-06' (unpatented).

Plant:

*Propagation*.—Meristem tissue culture obtained from young leaves.

*Root description*.—Fleshy creamy colored roots with small hairy lateral roots having yellow colored root tips.

*Time to produce a finished flowering plant*.—32 to 36 weeks after planting in a 12 cm (diameter) pot.

*Growth habit*.—Upright.

*Height* (*measured from soil, including inflorescence*):—27.0 cm to 32.0 cm.

*Width* (*measured from leaf tips*).—32.0 cm to 34.0 cm.

Leaves:

*Immature leaves*.—Length: 13.0 cm to 15.0 cm. Width: 8.0 cm to 9.0 cm. Color: Upper surface: RHS 146A. Lower surface: RHS 146B. Texture (both upper and lower surfaces): Shiny.

*Mature leaves*.—Length (fully expanded): 16.0 cm to 18.0 cm. Width: 10.0 cm to 11.0 cm. Shape: Ovate cordate. Apex: Acute. Base: Cordate. Leaf blade angle with the petiole: Between 110 degrees and 130 degrees. Leaf margin: Entire. Color: Upper surface: RHS 147A. Lower surface: RHS 147B. Texture (both upper and lower surfaces): Shiny. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Present. Arrangement: Leaf blade has two small lobes extending past the petiole. The lobes are non-touching. Length of lobes of mature leaf blades: 1.5 cm to 2.0 cm. Width of lobes of mature leaf blades: 3.5 cm to 4.5 cm. Distance from petiole/leaf junction to highest point on lobes of mature leaf: 3.5 cm to 4.5 cm.

*Petiole*.—Cross-section: Round. Diameter: 0.3 cm to 0.4 cm. Length: 12.0 cm to 14.0 cm for a mature leaf size. Color: Mature leaf: RHS 144A. Immature leaf: RHS 144B. Cataphyll color surrounding the petiole: Outside: RHS 145B. Inside: RHS 145D.

*Geniculum*.—Length: 1.5 cm to 2.0 cm. Width: 0.4 cm to 0.5 cm. Color: RHS 144A.

Inflorescence:

*Arrangement*.—Single.

*Flowering habit* (*length of flowering season*).—Continuous.

*Number of inflorescences per plant*.—6 to 8.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 80 degrees and 100 degrees; the spathe stands on a wiry peduncle about 5.0 cm to 7.0 cm above the foliage.

*Shape*.—Ovate.

*Apex*.—Acuminate.

*Base*.—Truncate.

*Texture* (*both upper and lower surfaces*).—Shiny.

*Margin*.—Undulated.

*Size*.—Length: 8.0 cm to 9.0 cm. Width: 7.0 cm to 7.5 cm.

*Lobes*.—Absent.

*Blistering*.—Weak.

*Color*.—When opening: White (RHS NN155C) with light pink shade (RHS 50D) and slightly green margins (RHS 145B to 145C) toward the base. Spathe has pink edge (RHS 50B). When fading: Upper surface: Pink (RHS 50C), green margins (RHS 144A) toward the base and dark green veins (RHS 147A). Lower surface: Light pink (RHS 49D), green margins (RHS 144B) toward the base and green veins (RHS 146A). After one year: Green (RHS 146B) at the base and lighter green (RHS 145C) with pink shade (RHS 51C) toward the tip.

*Venation color* (*after opening*).—Upper surface: RHS 50C. Lower surface: RHS 50D.

Peduncle:

*Shape*.—Erect.

*Cross-section*.—Round.

*Length*.—19.0 cm to 22.0 cm.

*Diameter*.—0.3 cm to 0.4 cm.

*Color*.—RHS 144B.

Flowering time:

*General*.—One small, rooted, untreated tissue culture plant of 8.0 cm tall will flower, depending on the season, after 32 to 36 weeks and 6 to 7 blossoms appear. More blossoms appear after some additional weeks so that a full flowering and commercial plant will have 7 to 8 white spathes. Smaller blossoms may occur on immature plants.

Spadix:

*Size*.—Length: 3.0 cm to 4.0 cm (depending on flower size). Width (at apex): 0.5 cm to 0.6 cm. Width (at base): 0.6 cm to 0.7 cm.

*Shape*.—Columnar.

*Angle from spadix tip to peduncle*.—150 degrees to 160 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 166B to 166C. Mature: RHS 186D. Ages to: RHS 152C.

Flowers:

*Quantity per spadix*.—150 to 200.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 182C.

Reproductive organs:

*Stamens*.—Not visible.

*Pollen amount*.—Absent.

*Pistil*.—Quantity: Many. Length: Less than 0.01 cm. Color: RHS 182C.

*Style*.—Not observed to date.

*Stigma*.—Shape: Ovoid. Diameter: Less than 0.01 cm. Color: RHS 182C.

*Ovary*.—Rarely visible.

*Ovary color*.—Not measured.

Fruit and seed set: None observed to date.

COMPARISON WITH PARENTAL AND COMMERCIAL VARIETIES

'ANTHYQDAL' differs from the female parent plant 'ANTHEPEDI' (U.S. Plant Pat. No. 18,644) in that 'ANTHYQDAL' has a spathe upper surface main color of white, a reddish brown immature spadix, and a purplish pink mature spadix, whereas 'ANTHEPEDI' has a spathe upper surface main color of red, a green-yellow immature spadix, and a white mature spadix.

'ANTHYQDAL' differs from the male parent plant '632-06' (unpatented) in that 'ANTHYQDAL' has a reddish brown immature spadix, a purplish pink mature spadix, a cordate spathe shape, and an ovate cordate leaf shape, whereas '632-06' has a light yellow green immature spadix, a yellowish white mature spadix, an ovate spathe shape, and a deltoid leaf shape.

'ANTHYQDAL' differs from similar commercial variety 'ANTHFOFUN' (U.S. Plant Pat. No. 30,527) in that 'ANTHYQDAL' has a wavy spathe with an acuminate apex and an upper surface main color of white, whereas 'ANTHFOFUN' has a flat spathe with a mucronate apex and an upper surface main color of light yellow and pink.

'ANTHYQDAL' differs from similar commercial variety 'ANTHCOTDOK' (unpatented) in that 'ANTHYQDAL' has a wavy spathe with an acuminate apex and an upper surface main color of white, whereas 'ANTHCOTDOK' has a slightly cupped spathe with a mucronate apex and an upper surface main color of yellowish pink.

I claim:

1. A new and distinct variety of *Anthurium* plant named 'ANTHYQDAL', substantially as illustrated and described herein.

* * * * *